US00PP29985P3

(12) United States Plant Patent
Kordes

(10) Patent No.: US PP29,985 P3
(45) Date of Patent: Dec. 18, 2018

(54) MINIATURE ROSE PLANT NAMED 'KORAROMA05'

(50) Latin Name: *Rosa hybrida*
Varietal Denomination: KORaroma05

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 16 days.

(21) Appl. No.: 15/731,504

(22) Filed: Jun. 20, 2017

(65) Prior Publication Data

US 2017/0374773 P1 Dec. 28, 2017

Related U.S. Application Data

(60) Provisional application No. 62/493,173, filed on Jun. 23, 2016.

(51) Int. Cl.
*A01H 5/02* (2018.01)
*A01H 6/74* (2018.01)

(52) U.S. Cl.
USPC ..... Plt./121
CPC ..... *A01H 5/02* (2013.01); *A01H 6/749* (2018.05)

(58) Field of Classification Search
USPC ..... Plt./121
See application file for complete search history.

(56) References Cited

PUBLICATIONS

UPOV hit on miniature rose plant named 'KORamoma05', QZ PBR 48562, filed Jun. 28, 2016.*

* cited by examiner

*Primary Examiner* — Anne Marie Grunberg
(74) *Attorney, Agent, or Firm* — Samuel R. McCoy, Jr.

(57) ABSTRACT

'KORaroma05' is a new and distinct variety of *Rosa hybrida* which is characterized by the combination of a compact growth habit with a moderately vigorous rate of growth, above average resistance to many rose diseases, solitary pastel pink flowers, double flowers, and strongly fragrant flowers. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination:

The inventive variety of *Rosa hybrida* disclosed herein has been given the variety denomination 'KORaroma05'.

STATEMENT REGARDING PRIOR DISCLOSURES BY THE INVENTOR UNDER 37 C.F.R. 1.77(B)(6)

The first public disclosure of the claimed plant was made in January of 2016 at the 2016 IPM horticulture tradeshow in Essen, Germany where it was displayed by the inventor amongst a collection of other rose cultivars. The claimed plant was not specifically identified by name in the display. 'KORaroma05' was not publically available or sold prior to one year before the date of the instant application.

BACKGROUND OF THE INVENTION

Parentage: The *Rosa hybrida* variety 'KORaroma05' is the result of a controlled cross-pollination breeding program carried out by the inventor in Klein Offenseth-Sparrieshoop, Germany. The objective of the said breeding program was to create a new and distinct rose plant with unique qualities, such as:

1. A compact growth habit and uniform flowering when grown as a potted floral plant; and
2. Abundant, long-lasting, fragrant and recurrent pastel pink flowers; and
3. Attractive foliage; and
4. Resistance to diseases encountered in greenhouse and nursery culture.

This combination of qualities is not present in prior rose cultivars known to the inventor. These objectives have been substantially achieved and in that distinguish 'KORaroma05' from all other varieties known to the inventor.

'KORaroma05' is a seedling selection which resulted from the controlled pollination of an unnamed *Rosa hybrida* seedling developed and owned by the same inventor (not protected), the seed parent, with a second unnamed *Rosa hybrida* seedling developed and owned by the same inventor (not protected), the pollen parent, during the summer of 2012. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2013 from the seedling beds due to its superior characteristics and asexually propagated for further evaluation. This new and distinctive rose variety was given the name 'KORaroma05'.

Asexual Reproduction: 'KORaroma05' was first asexually propagated by rooting vegetative cuttings in June of 2013 at the inventor's nursery in Klein Offenseth-Sparrieshoop, Germany. Subsequently, 'KORaroma05' has been successfully propagated by stem cuttings in Jackson County, Oreg. These initial and other subsequent propagations conducted in controlled environments demonstrate that 'KORaroma05' reproduces true to type in successive generations of asexual reproduction.

SUMMARY OF THE INVENTION

The following characteristics have been repeatedly observed and represent the distinguishing characteristics of the new *Rosa hybrida* cultivar 'KORaroma05'. These traits, in combination, distinguish 'KORaroma05' as a new and distinct cultivar.

1. *Rosa hybrida* 'KORaroma05' exhibits a moderately vigorous growth rate; and
2. *Rosa hybrida* 'KORaroma05' exhibits a compact growth habit; and
3. *Rosa hybrida* 'KORaroma05' exhibits above average resistance to powdery mildew and *Botrytis* diseases; and
4. *Rosa hybrida* 'KORaroma05' exhibits solitary pastel pink flowers which are held upright; and
5. *Rosa hybrida* 'KORaroma05' exhibits double flowers of a medium size for a miniature rose; and
6. *Rosa hybrida* 'KORaroma05' exhibits flowers with strong fragrance.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORaroma05', taken from a one year old plant.

DETAILED BOTANICAL DESCRIPTION

The following is a detailed botanical description of a new and distinct variety of *Rosa hybrida* known as 'KORaroma05', based upon observations made in October of 2016 from one year old, greenhouse-grown container plants in Jackson County, Oreg. Those skilled in the art will appreciate that certain characteristics will vary with older or, conversely, with younger plants. 'KORaroma05' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2001 edition except where common terms of color are used.

A botanical description of 'KORaroma05' and comparisons with the parents and closest known comparator variety of *Rosa hybrida* are provided below.

General plant description:

*Growth rate.*—Moderately vigorous.

*Growth habit.*—Compact.

*Mature dimensions.*—25 cm tall and 20 cm wide, when grown as a 10 to 15 cm pot plant.

*Cold hardiness.*—Unknown.

*Propagation.*—Stem cuttings and bud grafting.

*Disease resistance.*—Above average resistance to powdery mildew (*Sphaerotheca pannosa*) and *Botrytis* sp. diseases under normal greenhouse growing conditions in Jackson County, Oreg.

Root system:

*Type.*—Fibrous root system, with many root hairs.

*Branching.*—Moderately branched.

*Density.*—Moderately dense.

*Distribution.*—Roots distributed evenly throughout the soil profile, from shallow to deep.

Stems:

*Stem color.*—Young stems are Yellow-Green Group 146A; mature stems are Yellow-Green Group 146A.

*Anthocyanin intonations.*—Intonations of Greyed-Purple Group 183C are limited to the distalmost portion of the juvenile stems, below inflorescences.

*Stem surface texture.*—Both young stems and mature stems are smooth.

*Stem dimensions.*—Typical mature stems are approximately 10 to 20 cm long and 2.0 to 4.0 mm in diameter.

*Prickles.*—Incidence — Typically 1 to 3 prickles per 10 cm of stem, on average. Size — Average length is 2.0 to 3.0 mm long. Immature prickle color — Greyed-Purple Group 184B and suffused with Greyed-Purple Group 183B. Mature prickle color — Greyed-Purple Group 183C and senescing to Greyed-Brown Group N199D. Shape — Concave. Texture — Smooth.

Leaves:

*Arrangement.*—Imparipinnate compound leaves; mature axillary leaves typically with 5 leaflets on normal leaves in the middle of the stems.

*Attachment.*—Petiolate.

*Dimensions.*—95 to 110 mm long and 73 to 86 mm wide.

*Abundance.*—Very abundant; normally with 25 to 30 leaves.

*Stipules.*—Size — 11 mm long and 6.0 to 7.0 mm wide. Stipule color — Yellow-Green Group 146B. Anthocyanin intonations — Greyed-Purple Group 183C; mostly present on juvenile foliage. Stipitate glands — Abundant along the margins. Margins — With stipitate glands. Texture, adaxial surfaces — Lightly pubescent. Texture, abaxial surfaces — Glabrous. Apex — Aristate. Base — Fused to the petiole.

*Petiole.*—Length — Average 11 to 12 mm. Diameter — Average 1.0 mm. Petiole color, adaxial surface — Yellow-Green Group 146B. Petiole color, abaxial surface — Yellow-Green Group 146B. Anthocyanin intonations — Greyed-Purple Group 184C on juvenile foliage; the presence of Greyed-Purple Group 184C intonations is variable on mature foliage. Margins — With a limited number of stipitate glands. Prickles — None present. Stipitate glands — Variable; ranging from a limited number of glands to moderately abundant. Texture — Lightly pubescent. Strength — Strong.

*Rachis.*—Length — Average 17 to 18 mm. Diameter — Average 1.0 mm. Color — Yellow-Green Group 146B. Anthocyanin intonations — Greyed-Purple Group 183C on juvenile foliage; the presence of Greyed-Purple Group 183C intonations is variable on mature foliage. Margins — With a limited number of stipitate glands. Prickles — A few small prickles on the abaxial surface. Stipitate glands — A limited number of stipitate glands are present along the margins. Texture — Glabrous.

*Leaflets.*—Dimensions — Average size of the terminal leaflet is 39 to 51 mm long and 20 to 25 mm wide. Shape — Ovate. Apex — Acute. Base — Obtuse. Margins — Finely serrated; no undulation. Texture, pubescence, and luster; adaxial surface — Leathery, glabrous, and semi-glossy. Texture, pubescence, and luster; abaxial surface — Leathery, glabrous, and matte. Stipitate glands — A limited number of stipitate glands are present along the abaxial midrib and margins. Juvenile foliage color, adaxial surface — Yellow-Green Group 147A. Juvenile foliage color, abaxial surface — Yellow-Green Group 147B. Mature foliage color, adaxial surface — Yellow-Green Group 147A. Mature foliage color, abaxial surface — Yellow-Green Group 147B. Anthocyanin intonations — Intonations of Greyed-Purple Group 183C are present on the adaxial and abaxial surfaces of the juvenile foliage, and also at and near margins of mature foliage. Venation — Reticulate. Petiolule — Dimensions — 2.0 mm long and 1.0 mm in diameter. Petiolule color, adaxial surface — Yellow-Green Group 147B. Petiolule color, abaxial surface — Yellow-Green Group 147B. Prickles — None observed. Margins — A few stipitate glands are present. Texture, adaxial surface — Smooth. Texture, abaxial surface — Smooth.

Inflorescence:

*Inflorescence type.*—Flowers are solitary. Flowers are held upright.

*Blooming habit.*—Recurrent.

*Size.*—140 mm tall and 60 mm wide, on average.

Flowering laterals: Present below the initiation of inflorescence. Generally 1 flowering lateral is present, with 1 flower per flowering shoot.

Flower bud:

*Bud form.*—Long; pointed ovoid to high centered.

*Size.*—Upon opening, 38 mm in length from base of receptacle to distal end of bud and 12 to 14 mm diameter at its widest point.

*Texture.*—Smooth.

*Color, as sepals first unfold.*—Red-Purple Group 61C.

*Color when one-quarter open, inner side.*—Marginal Zone — Red-Purple Group N66A. Middle Zone — Nearest to a combination of Red-Purple Group 63D and Red-Purple Group N66A. Basal Zone — Nearest to a combination of Red-Purple Group 63D and Red-Purple Group N66A.

*Color when one-quarter open, outer side.*—Marginal Zone — Red-Purple Group N66A. Middle Zone — Red-Purple Group N66A. Basal Zone — Red-Purple Group N66A.

Flower:

*Peduncle.*—Length — 30 to 40 mm average length. Diameter — 1.0 to 2.0 mm average diameter. Color — Yellow-Green Group 146A. Anthocyanin intonations — Greyed-Purple Group 183B. Strength — Somewhat strong. Surface — Smooth with fine hairs and stipitate glands.

*Calyx.*—General — Comprised of five polysepalous sepals, with weak foliaceous appendages present on three sepals. Diameter of calyx — 65 to 70 mm, at anthesis. Sepals — Color, upper surface — Yellow-Green Group 144A. Color, lower surface — Yellow-Green Group 144A. Anthocyanin intonations — Greyed-Purple Group 183B present at the apex of foliaceous appendages and variable along the abaxial midrib. Size — 30 mm long and 6 to 11 mm wide, on average. Apex — Apiculate. Base — Flat at union with receptacle. Quantity — Five. Upper surface — Lightly pubescent. Lower surface — Smooth. Margins — Pubescent; stipitate glands are present. Stipitate glands, occurrence — Limited.

*Corolla.*—Conformation — Double. General shape of corolla — Round. Shape of corolla when viewed from the side — Upon opening, upper portion — Flat. Upon opening, lower portion — Flattened convex. Open flower, upper portion — Flat. Open flower, lower portion — Flattened convex. Dimensions — Medium size for a miniature rose. When open, the average flower diameter is 55 to 60 mm and the average flower height is 30 to 35 mm. Fragrance — Strong. Duration — On the plant for 12 to 14 days. Senesced petals drop away cleanly. Petals — Petal count — Exhibits double flowers with an average of 25 petals under normal conditions. Petal reflex — Petals are slightly reflexed. Timing of petal reflex — One by one. Petal margin — Entire; not undulated. Petal shape — Obovate. Apex — Obtuse. Base — Obtuse. Dimensions — 27 to 34 mm long and 16 to 33 mm wide. Texture, inner surface — Smooth. Texture, outer surface — Smooth. Petal color, upon opening — Outermost petals, inner surface — Marginal Zone — Red-Purple Group N66A. Middle Zone — Nearest to a combination of Red-Purple Group 63D and Red-Purple Group N66A. Basal Zone — Nearest to a combination of Red-Purple Group 63D and Red-Purple Group N66A. Outermost petals, outer surface — Marginal Zone — Red-Purple Group N66A. Middle Zone — Red-Purple Group N66A. Basal Zone — Red-Purple Group N66A. Innermost petals, inner surface — Marginal Zone — Red-Purple Group 63C. Middle Zone — Nearest to a combination of Red-Purple Group 63C and Orange-White Group 159D. Basal Zone — Nearest to a combination of Red-Purple Group 63C and Orange-White Group 159D. Innermost petals, outer surface — Marginal Zone — Red-Purple Group 63C. Middle Zone — Red-Purple Group 63C. Basal Zone — Red-Purple Group 63B. Basal petal spots, upon opening — No distinctive coloration at the petal base. Petal color, after opening — Outermost petals, inner surface — Marginal Zone — Red-Purple Group 63B. Middle Zone — Red-Purple Group 63C. Basal Zone — Red-Purple Group 63C. Outermost petals, outer surface — Marginal Zone — Red-Purple Group 63B. Middle Zone — Red-Purple Group 63B. Basal Zone — Red-Purple Group 63B. Innermost petals, inner surface — Marginal Zone — Red-Purple Group 63D. Middle Zone — Nearest to a combination of Red-Purple Group 63D and Orange-White Group 159D. Basal Zone — Nearest to a combination of Red-Purple Group 63D and Orange-White Group 159D. Innermost petals, outer surface — Marginal Zone — Red-Purple Group 63D. Middle Zone — Red-Purple Group 63D. Basal Zone — Red-Purple Group 63B. Basal petal spots, after opening — No distinctive coloration at the petal base. General Tonality — On open flower, Red-Purple Group N66A. No change in general tonality at the end of the fourth day; thereafter the general tonality is Red-Purple Group 63C. Petaloids — Quantity — 8 petaloids per flower, on average. Dimensions — Variable; approximately 20 to 22 mm long and 7.0 to 13 mm wide. Color, inner surface — Marginal Zone — Red-Purple Group 63C. Middle Zone — Red-Purple Group 63C, with an Orange-White Group 159D central longitudinal stripe. Basal Zone — Red-Purple Group 63C, with an Orange-White Group 159D central longitudinal stripe. Color, outer surface — Red-Purple Group 63C, with an Orange-White Group 159D central longitudinal stripe from base to apex. Margins — Indented. Shape — Obovate. Apex — Obtuse to emarginate. Base — Cuneate. Texture, inner and outer surfaces — Smooth.

Reproductive organs:

*Stamens.*—Quantity — Approximately 80, on average, arranged around the styles. Anthers — Shape — Reniform. Dimensions — 2.0 mm long and 1.0 mm wide, on average. Color — Greyed-Yellow Group 162A. Pollen — Absent. Filaments — Color — Greyed-Purple Group 184D. Length — 6.0 mm.

*Pistils.*—Quantity — Average; approximately 40. Stigmas — Size — Less than 1.0 mm long and 1.0 mm wide. Location — Inferior in position to anthers. Color — Greyed-Yellow Group 161D. Styles — Length — Approximately 5.0 to 7.0 mm long. Color — Greyed-White Group 157B, with intonations of Greyed-Purple Group 184D. Ovary — Dimensions — 8.0 mm long and 6.0 mm in diameter. Color — White Group 155C.

*Receptacle.*—Shape — Urn-shaped. Dimensions — Approximately 8.0 to 11 mm high and 7.0 to 10 mm wide. Color — Yellow-Green Group 144A. Texture — Smooth with a few fine hairs.

Hips and seed formation: Not observed.

Comparisons With the Parents

The new rose plant may be distinguished from its seed parent, an unnamed *Rosa hybrida* seedling, by the following combination of characteristics:

1. 'KORaroma05' exhibits fewer flower petals than the seed parent.
2. 'KORaroma05' exhibits smaller flowers than those of the seed parent.
3. 'KORaroma05' exhibits pastel pink flowers, whereas the seed parent exhibits darker pink flowers.

The new rose plant may be distinguished from its pollen parent, an unnamed *Rosa hybrida* seedling, by the following combination of characteristics:

1. 'KORaroma05' exhibits pastel pink flowers, whereas the pollen parent exhibits white flowers.
2. 'KORaroma05' exhibits smaller flowers than those of the pollen parent.
3. 'KORaroma05' exhibits a moderately long shelf life as a potted plant, whereas the pollen parent exhibits a short shelf life as a potted plant.

Comparison With the Most Similar *Rosa* Cultivar Known to the Inventor

For a comparison, several physical characteristics of the *Rosa hybrida* variety 'KORdatiffi' (not patented in the United States; Community Plant Variety Office grant number 31768), a rose variety from the same inventor, are compared to 'KORaroma05' in Chart 1.

CHART 1

| Characteristic | 'KORaroma05' | 'KORdatiffi' |
|---|---|---|
| Petal count. | 25 petals. | Approximately 30 to 40 petals. |
| Petaloids. | 8 petaloids. | Approximately 30 to 40 petaloids. |
| General tonality of the flower, at anthesis. | Red-Purple Group N66A. | Red Group 62B. |
| Fragrance. | Strong. | None. |

That which is claimed:

1. A new and distinct variety of rose plant named 'KORaroma05', as described and illustrated herein.

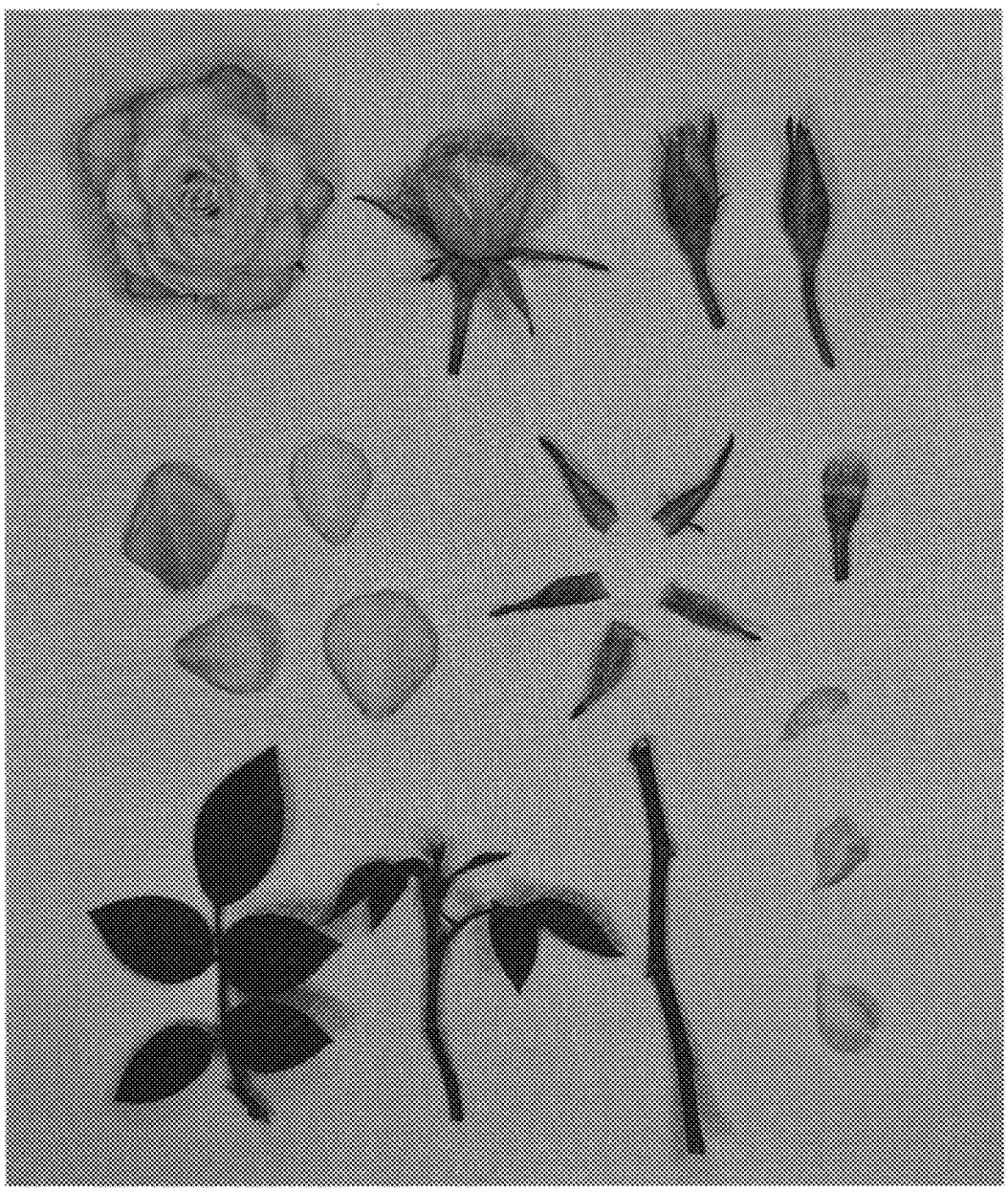

* * * * *